United States Patent [19]

Rooney et al.

[11] Patent Number: 5,603,414
[45] Date of Patent: Feb. 18, 1997

[54] DETECTING DIAMONDS IN A ROCK SAMPLE

[75] Inventors: Marie-Line Rooney, Maidenhead; James G. C. Smith, HIgh Wycombe; Martin P. Smith, Wargrave; Martin Cooper, Marlow, all of England

[73] Assignee: Gersan Establishment, Vaduz, Liechtenstein

[21] Appl. No.: 343,525
[22] PCT Filed: May 28, 1993
[86] PCT No.: PCT/GB93/01127
  § 371 Date: Jan. 25, 1995
  § 102(e) Date: Jan. 25, 1995
[87] PCT Pub. No.: WO93/24833
  PCT Pub. Date: Dec. 9, 1993

[30] Foreign Application Priority Data

Jun. 3, 1992 [GB] United Kingdom .................. 9211734

[51] Int. Cl.⁶ ............................................. B07C 5/00
[52] U.S. Cl. ........................................ 209/588; 209/589
[58] Field of Search ............................... 209/2, 7, 9, 3, 209/3.1, 589, 578, 588

[56] References Cited

U.S. PATENT DOCUMENTS

| | | | |
|---|---|---|---|
| 2,717,693 | 9/1955 | Holmes | 209/578 X |
| 4,212,397 | 7/1980 | Bockelman | 209/589 X |
| 4,365,719 | 12/1982 | Kelly | 209/589 |
| 4,653,081 | 3/1987 | Sipila et al. | 209/589 X |
| 5,076,502 | 12/1991 | Kitaguchi et al. | 209/589 X |
| 5,206,699 | 4/1993 | Stewart et al. | 209/589 X |

FOREIGN PATENT DOCUMENTS

| | | | |
|---|---|---|---|
| 0341094 | 11/1989 | European Pat. Off. | 209/589 |
| 2013335 | 1/1979 | United Kingdom . | |
| 2056056 | 6/1980 | United Kingdom . | |
| 2067753 | 1/1981 | United Kingdom . | |
| 2073410 | 2/1981 | United Kingdom . | |
| 2107861 | 10/1982 | United Kingdom . | |
| 2121535 | 12/1983 | United Kingdom | 209/589 |

OTHER PUBLICATIONS

B. W. Anderson, GEM Testing, Jan. 1942, (3 pages), Butterworth & Co. (Tenth Edition).

*Primary Examiner*—D. Glenn Dayoan
*Attorney, Agent, or Firm*—Cesari and McKenna

[57] ABSTRACT

In order to provide secure and simple detection of diamonds when prospecting, a rock sample is reduced to powder particles which are automatically checked to see if they contain diamond particles (30) by processing an image of X-radiation transmitted through a layer of the particles. The image may be processed by comparing it with a further image of visible light transmitted by the layer of particles.

30 Claims, 5 Drawing Sheets

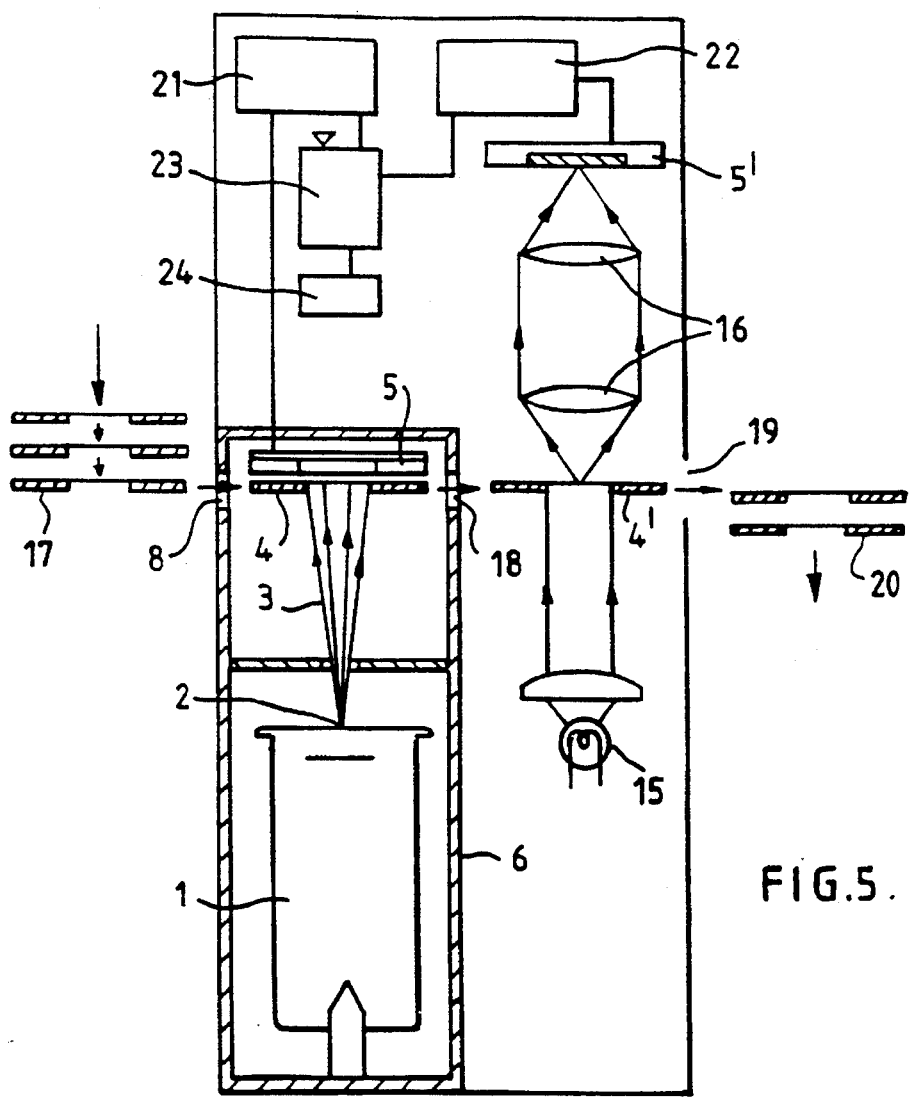
FIG. 5.
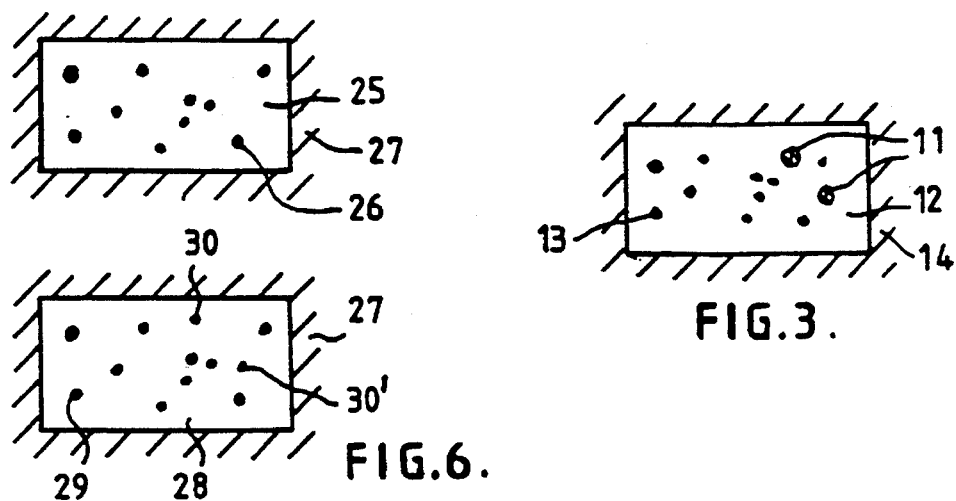
FIG. 6.
FIG. 3.

DETECTING DIAMONDS IN A ROCK SAMPLE

BACKGROUND OF THE INVENTION

The present invention relates to a method of and apparatus for detecting diamonds in a rock sample, and can be used when prospecting for diamonds to locate microdiamonds in particulate mineral material.

When prospecting for diamonds, samples of rock, e.g. drill cores, are taken and are reduced to powder particles (particle size generally in the range from 50 to 300 micrometers), e.g. by chemical treatment and grinding. This mineral powder is analyzed by taking samples and spreading the samples on microscope slides, which are then observed under a microscope by a skilled operator.

The rock samples may contain diamonds, usually in a very low concentration, and these will give rise to small diamonds or fragments of diamond—microdiamonds—in the powdered mineral sample. Thus diamondiferous rock may be identifiable by the presence of microdiamonds in the mineral powder samples.

Detecting microdiamonds in mineral powder samples is a very skilled job and very time consuming. The microdiamonds themselves may be graphite covered and very difficult to recognize. In most cases, there will be no microdiamonds in a sample, and a very large number of samples has to be processed as part of the prospecting process.

It is an object of the present invention to provide a method of and apparatus for detecting diamonds in a rock sample whereby diamond can be identified uniquely. It is also an object of the present invention to provide a method of and apparatus for detecting diamonds in a rock sample which can be carried out automatically by a machine.

SUMMARY OF THE INVENTION

The present invention provides a method of and apparatus for ascertaining whether diamonds (ie., particles comprising diamond material) are present in a layer of powder particles obtained by reducing a rock sample and placing (normally depositing) the powder particles on a substrate.

The invention exploits the relative transparency of diamond material to soft (i.e. relatively low energy) X-radiation compared with other material. Powder particles which transmit X-radiation, or only absorb a small amount of X-radiation are identified as probably diamond. The location of the diamonds in the sample may also be identified, and the weight of the diamonds present may be estimated. The powder particles may be identified as being diamond or not.

Diamond is found to have relatively high transparency to soft X-radiation compared with all other minerals with which diamonds are likely to be associated. This is due to the low atomic number of carbon, from which diamond is formed. All the other minerals present in the sample will contain a significant proportion of higher atomic number elements, such as aluminjure or silicon, which have significantly higher absorptions than diamond. The energy of X-rays used depends on the particle size, but will usually be about 8 keV.

Preferably, the layer of powdered mineral material is mounted on a standard soft X-ray transparent microscope slide, which forms said substrate.

Mineral powder may be prepared by crushing rock samples and treating the resulting powder in a similar process to that used in normal prospecting.

Although for convenience, the small particles are referred to herein as powder, the particles can be of a size normally considered to be grit rather than powder. The particles can typically be in the size range about 20 micrometers to about 600 micrometers, preferably about 50 micrometers to about 300 micrometers, but nonetheless the particles may have a size of up to about 1 mm or about 2 mm or more and could mainly be in the range about 1 mm to about 2 mm.

The apparatus of the invention may be set up to indicate which samples have microdiamonds, to give an indication of the location of the microdiamonds in the layer and, possibly, to indicate the size and weight of the diamonds identified. In order to do this, the image of X-radiation transmitted by the layer will have to be analyzed by an image processing technique. For example, the powder may be set up on a slide with defined corners, the image processing device being programmed to locate the corners of each image and to reference the positions of all particles identified accordingly.

The layer is preferably spread such that the radiation can pass between the particles to define a background in the image, and more particularly such that the particles in general are not in contact with each other, though some contacting particles are tolerable. Thus the particles will be dispensed in a layer on the substrate, and can be relatively, widely spaced in the layer. The layer is then substantially one particle in thickness in the direction of the incident radiation.

To image the transmitted radiation, the detector may be placed close behind the sample to form a shadow image, like a contact print. Other X-ray imaging apparatus may be used. The images will preferably comprise well defined spots of different intensity or greyness to the background. The spots preferably comprise dark spots (shadows cast by particles) on a lighter background; in this case, the "intensity" of a spot refers to its "greyhess" or "blackness". The spots may, of course, be light and the background dark, depending on the operation of the detector; in that case, the "intensity" of the spot would refer to its "whiteness". In each case, the "intensity" of a spot refers to the degree of contrast to the background. The image may be formed by scanning the sample.

In a first embodiment, a single observation of the powder particle layer may be made by using X-radiation such that diamonds absorb the X-radiation weakly and show up on the image as faint (low intensity) but clearly visible spots. The images will have a plurality of spots, spots corresponding to diamonds being of different intensity to other spots. These spots may be analyzed by image processing techniques in which the size of the spot is measured. The intensity of each spot on the image is then measured and corrected in relation to its size. The resulting measurement will depend upon the absorptivity of the particle represented by the spot, which will be low in the case of diamond and higher in the case of all other mineral material.

In further embodiments of the invention, the image of X-radiation transmitted by the layer may be compared to an image of other radiation transmitted by the layer. Both the first mentioned radiation and the further radiation may comprise a plurality of wavelengths, preferably a continuum of wavelengths, according to the type of source used. The further radiation should have a spectrum such that a greater proportion of the irradiating energy is at wavelengths which are more strongly absorbed by diamond than the first mentioned radiation.

For example, in a second embodiment, the further radiation may comprise visible light, infrared, ultraviolet or other suitable radiation. In a third embodiment, the further radiation comprises lower energy X-radiation than the first mentioned radiation, the lower energy X-radiation being more strongly absorbed by the diamonds. In both the second and third embodiments, diamonds will show up in the second image as clearly visible spots, but will not show up, or only very faintly, in the first image.

The first image and the second image may be compared identify particles which are present in the latter but not the former. These are identified as diamonds. Their size may be indicated by image processing techniques.

The volume of a microdiamond may be estimated using Image processing techniques by determining the white level in the region of the image containing the diamond and integrating the deviation of the intensity signal from that level over that region. The weight can then be determined from the volume. The system is first calibrated using a sample of known thickness.

The method of the invention does not rely upon expertise of skilled operators and allows a large number of samples to be processed relatively quickly and automatically.

The method of the invention provides a good distinction of diamond material from other mineral, using the relatively low absorption of X-radiation by diamond in a surprising manner.

By placing the detector very close behind the sample, geometric unsharpness effects due to the finite size of the X-ray source are minimized. The penumbra of the particles on the detector can be thereby minimized. The detector should be placed only a few millimeters behind the layer, preferably less than 1 millimeter.

In possible alternative embodiments, the operator may not be presented with an image but simply with an indication as to whether or not there are any microdiamonds in the sample and the estimated weight of each one. The sample may also be marked, e.g. with ink, to facilitate retrieving the microdiamonds for further examination.

The invention will be further described by way of example only with reference to the following drawings, in which:

BRIEF DESCRIPTION OF THE DRAWINGS

FIG. 3 shows an image obtained with the first embodiment of the invention;

FIG. 5 shows apparatus according to a second embodiment of the invention;

FIG. 6 Shows images obtained with the second embodiment of the invention; and

DESCRIPTION OF THE PREFERRED EMBODIMENT

The present invention exploits the relative transparency of diamond to soft X-radiation.

Figure 1:
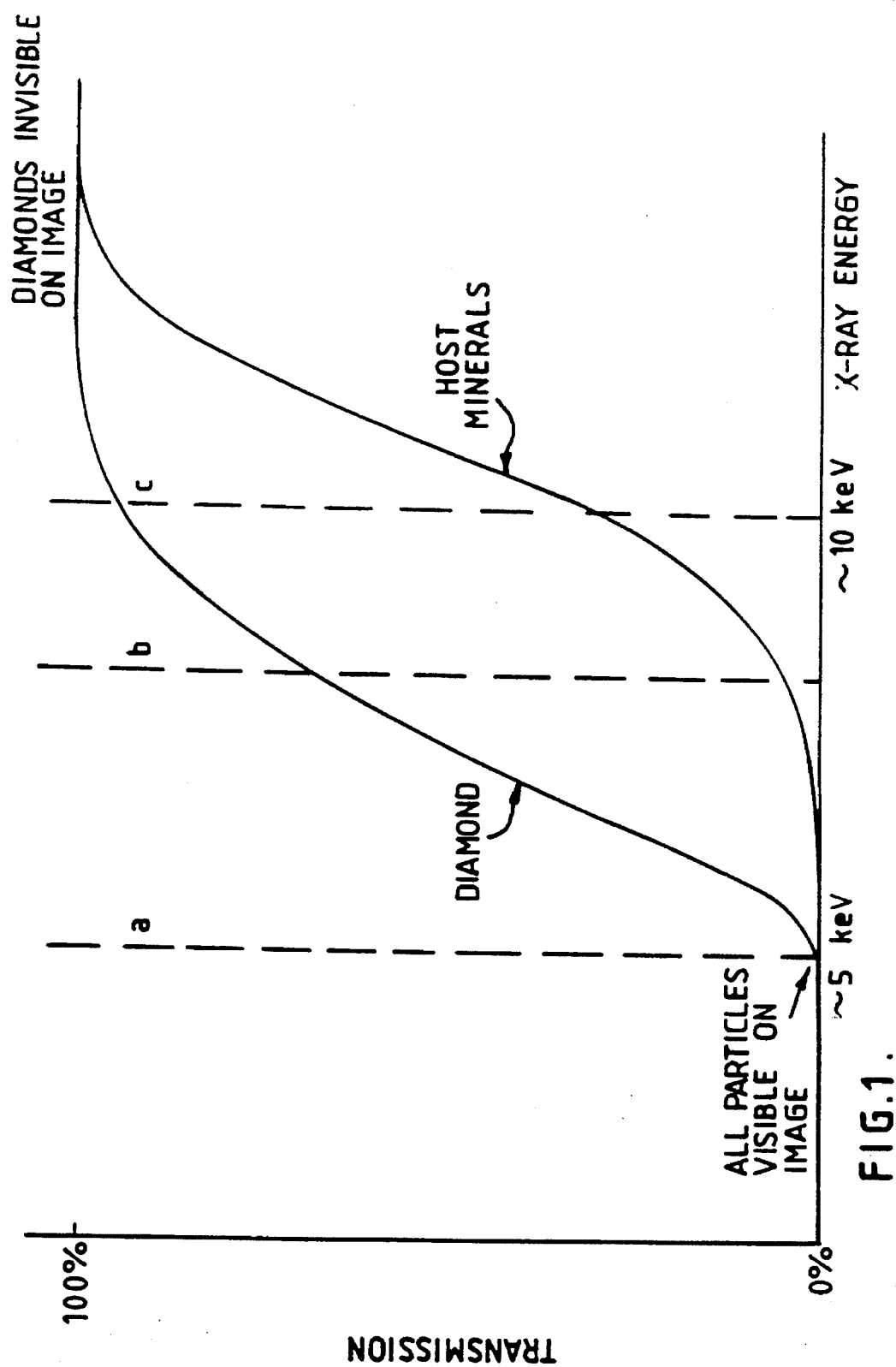
FIG. 1 is a graph showing the absorption of X-rays by diamond and other minerals.

FIG. 1 is a typical graph of the % of transmission of X-rays against X-ray energy for a diamond and for typical host-mineral. The shape of the graph will vary with diamond particle size, but is representative. For very soft. X-rays, at (a), in this case below 5 keV, host-mineral and diamond both show low to zero transmission.

At higher energy, for example at (b) on the graph, the transmission of X-rays by diamond is significantly higher than host-mineral.

At still higher energies, at (c), diamond is substantially transparent to X-rays. The actual X-ray energy corresponding to (c) varies with the size of the diamond. Typically, for the size of particle found in the powder samples, it will be around 10 keV.

Figure 2:
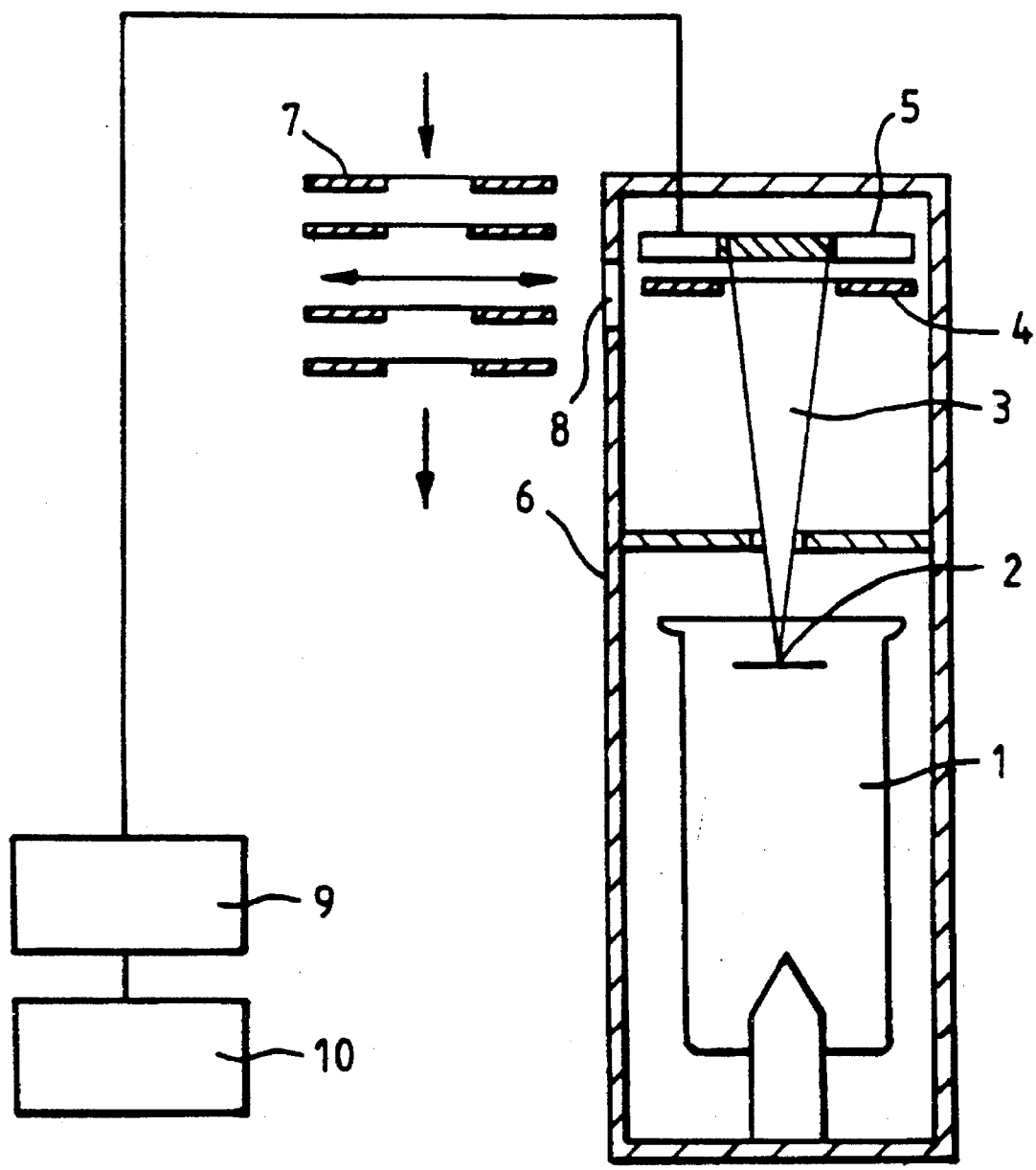
FIG. 2 shows an apparatus for irradiating a powder sample with X-radiation, for use with the present invention.

FIG. 2 shows an apparatus for exposing a sample of mineral powder particles to X-radiation, for forming an image of the X-radiation transmitted by the sample. The sample is prepared from rock samples which are crushed, chemically treated and graded in the manner normal in prospecting. A small sample of the powder particles thus obtained is mounted on a modified slide projector type slide, e.g. by allowing the powder particles to fall onto adhesive tape secured to the slide with a sticky side uppermost. A small central portion of the slide (for example, a square side approximately 12 millimeter) is used and the rest of the slide is masked off using metallic tape. The metallic tape is opaque to light and X-rays and provides a reference for the position of objects on the slide.

The apparatus comprises an X-ray source 1 comprising a normal X-ray tube, with a focal spot indicated at 2. X-radiation 3 is transmitted onto slide 4, illuminating the part of the slide 4 on which the powdered mineral sample is retained. The mineral particles either transmit, absorb slightly or absorb strongly the X-radiation and the resulting image of X-radiation transmitted by the sample is formed on a detector 5. The detector may be an X-ray sensitive vidicon tube or silicon CCD camera chip or other suitable detector which senses the transmitted X-rays. Images obtained from the camera may be averaged over a number of frames to enhance image quality.

The detector 5 is placed very close behind the sample. The X-rays emanating from the focal spot 2 do not emanate from a point source—the focal spot is of finite size, for example 100 to 500 millimeter. Accordingly, the images formed on the detector 5 will be fuzzy, due to a penumbra effect. This penumbra effect is minimized by having the detector 5 very close to the sample 4.

The whole device is enclosed in a casing 6 which prevents harmful X-radiation leaking out of the apparatus. There is a magazine of substrates or slides 7 which are fed one at a time into the viewing zone through aperture 8 in the casing 6. In FIG. 2, slides 7 are fed from the top, each slide being fed into the viewing zone 8 when it reaches the appropriate position, analyzed and removed again. Slides 7 which have been analyzed are fed downwards towards the bottom of the magazine in order, so that they can be correlated with the images observed. The magazine may be a slide projector type magazine and contain slides in batches of 20 to 200, preferably 50 to 100. A shutter may be provided for closing aperture 8 when the sample is being irradiated.

Reference numeral 9 denotes a processor for processing the images produced on detector 5. Processor 9 is set up to process the image according to the first or second embodiment of the invention to identify diamond particles in the powdered sample. 10 indicates a memory or similar device for identifying the particles, their position on the sample, and, perhaps, their size and weight so that relevant samples can be picked out of the magazine and tested further. 10 may also include a display or a device for stopping the machine when diamonds have been identified.

FIG. 3 shows an image of the sample obtained using the first embodiment of the invention.

In the first embodiment of the invention, a single image of each sample 4 is taken using the device of FIG. 2. The X-radiation used is of such an energy (around 8 keV) that non-diamond mineral absorbs the X-radiation strongly and diamond powder absorbs X-radiation weakly. Accordingly, the diamonds will show up as faint spots 11 on the image 12 obtained from the apparatus of FIG. 2. Reference numeral 13 denotes non-diamond mineral grains.

Figure 4:
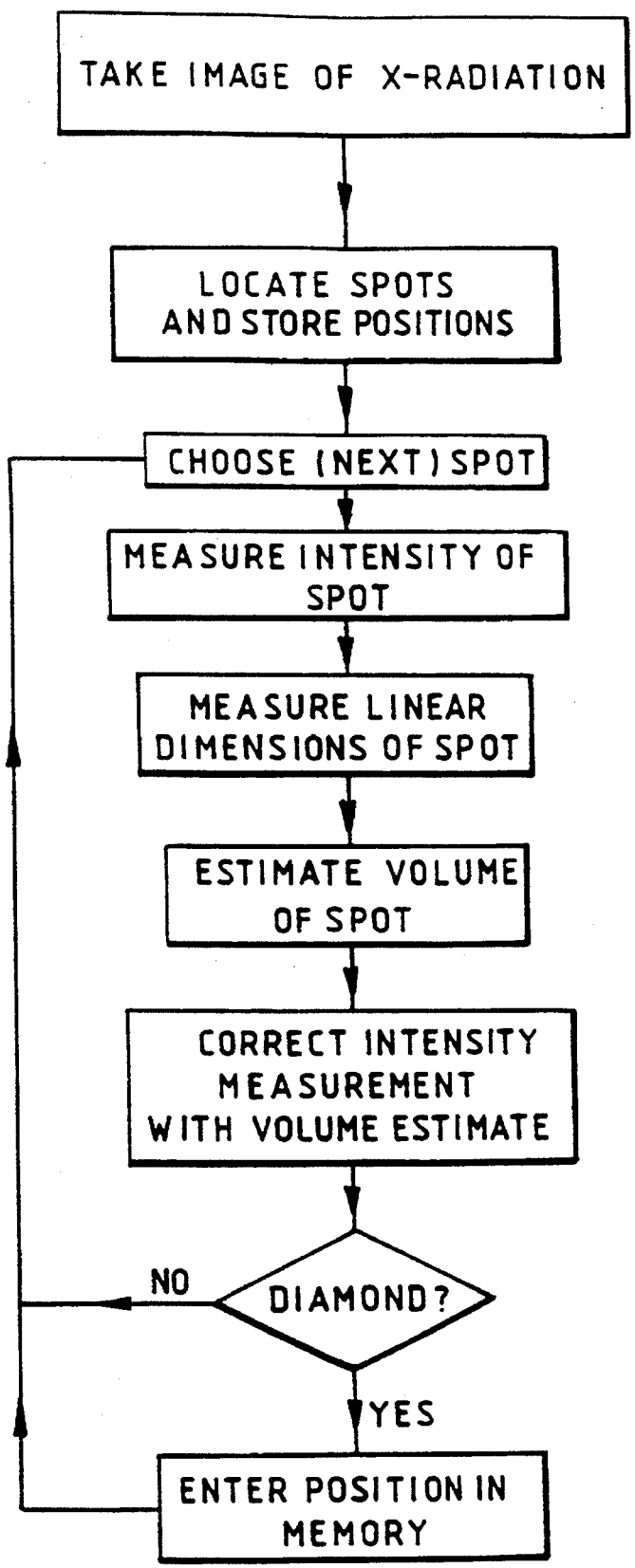
FIG. 4 is a schematic flow chart for the processor of the first embodiment.

Processor 9 detects the spots 11, formed by diamonds in the manner shown in FIG. 4. When the samples are set up, the boundaries of the sample are carefully defined with opaque material such as metallic tape, which forms the sharp boundaries 14. Processor 9 then produces a digital map of the images produced by the detector 5. Processor 9 searches for all spots (i.e. particles) in the image and stores their position. In this embodiment, processor 9 is programmed to sense the intensity of each spot 11 or 13, ie, the contrast with the background. In general, spots with low intensity will correspond to diamond. However, spots produced by very small non-diamond grains will also be faint whereas large diamond particles will give rise to relatively strong absorption as the path length of X-radiation through them is greater. Accordingly, processor 9 also measures the dimensions of a spot on image 12 and forms an estimate of the volume of the particle. The processor assumes that the path length is related to the linear dimensions of the spots on the image 12. This measurement is then used to correct the observations of intensity of spots to allow for size. Spots having a corrected intensity measurement which is lower than a given cut off level are identified as diamond and their presence (and maybe position) is stored in memory 10.

This embodiment allows an accurate estimate of the weight of any microdiamond present to be made. The intensity of any point on the image of a microdiamond is related to the thickness of the microdiamond at that point. The relationship between sample thickness and the amount of absorption for diamond depends on the energy spectrum of the X-ray source, and can be determined by using calibration samples of diamond of known dimensions. By integrating the fraction of X-rays absorbed by the microdiamond over the whole spot, and using the calibration, the volume of the microdiamond and hence its weight may be determined.

FIG. 5 shows apparatus according to a second embodiment of the invention for identifying diamonds in a powder sample.

The apparatus of FIG. 5 uses the X-ray irradiating device of FIG. 2, components of FIG. 5 corresponding to similar components in FIG. 2 having the same reference numerals.

In this embodiment of the invention, after the slide 4 has been irradiated with X-radiation 3 (of approximately 10–12 keV) and an image formed on detector 5, the slide 4 is passed to a second station in which it is illuminated with light from a source 15. In this case, the light is visible radiation; however, the light could be any suitable radiation which is strongly scattered or absorbed by diamonds. A slide 4' is shown illuminated with light, an image of the powder sample on the slide being formed by the optical system 16 on a detector 5'. Detector 5' may comprise a CCD camera chip. The samples may be illuminated by a low power lamp or LED source and a suitable condenser system. The optical system 16 works at approximately unit magnification.

The slides are retained in a magazine 17 in the apparatus of FIG. 5, being fed downwards until they reach aperture 8 where they are fed in turn to be illuminated with X-radiation. After an image of a slide 4 has been taken by detector 5, the slide 4 is passed through aperture 18 to the illuminating station so that an image of the sample in, for example, visible light may be taken by detector 5'. Thereafter, the slides are passed through aperture 19 to a further magazine 20 where they are collected in order. The images formed on detectors 5 and 5' are analyzed by processors 21 and 22 respectively. A further processor 23 compares the images produced by processors 21 and 22 to locate and further process diamond particles on the slide. A device 24 is provided to act as a memory for identifying slides on which diamonds were located.

In an alternative embodiment, after the irradiation with X-radiation, the slide 4 could be kept stationary and the X-ray source could be moved or left in position and visible light shone through the slide 4, e.g. using a fiber optic; the same detector 5 can be used for both observations. This avoids registration problems.

FIG. 6 shows the images of X-radiation transmitted by the sample and visible radiation transmitted by the sample obtained from detectors 5 and 5' respectively. Reference numeral 25 denotes the image of X-radiation transmitted by the sample. Spots 26 indicate particles which are substantially opaque to X-radiation. Any diamonds in the sample will not show up on image 25 and accordingly cannot be detected per se. Reference numeral 27 denotes the opaque material surrounding the illuminated portion of the slide, which acts as a position reference, as set out above. Reference numeral 28 denotes the image of visible radiation produced by detector 5'. Spots 29 corresponding to spots 26 are seen on the image 28, and are produced by the same particles as those seen on image 25. However, diamonds of powder size are substantially opaque to visible radiation (they may be very rough or covered in graphite) and will scatter light incident on them to provide shadows. Two diamonds, 30 and 30' are shown on image 28.

Figure 7:
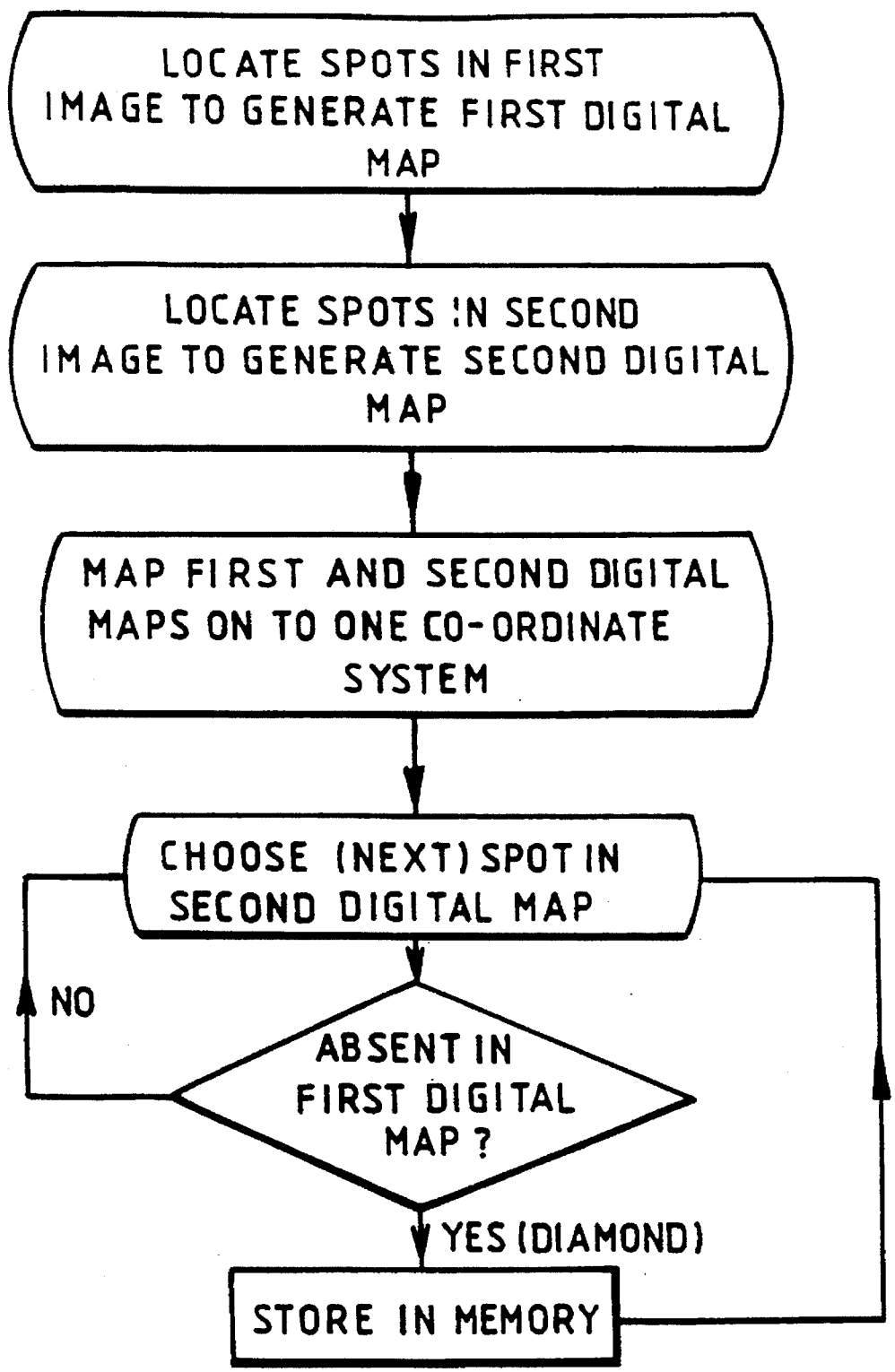
FIG. 7 is a schematic flow diagram for the processor of the second or third embodiment.

As set out in FIG. 7, processors 21 and 22 detect the spots 30 and 30' formed by diamonds in the following manner. The processors 21 and 22 produce digital maps of the images as in the first embodiment by locating spots and storing their positions. The two digital maps of the images are then mapped by the processor 23 onto the same coordinate system. The processor 23 checks whether each spot present in the second digital map is or is not present in the first digital map. Spots present in the second image but not in the first are identified as possible diamonds. This information is fed to memory 24.

The apparatus of FIG. 2 may be used to detect diamonds in the sample according to the third embodiment of the invention. In the third embodiment of the invention, no image of visible light transmitted from the sample is formed. Instead, after each sample has been irradiated with soft X-radiation at for instance 10 keV, the source 1 is altered to produce even softer (lower energy, approximately 5 keV) X-radiation (i.e. X-radiation in which the greater proportion of the energy is at longer wavelengths) which is more strongly absorbed by diamond. Accordingly, two images of each slide 4 are produced on detector 5 in turn and fed to processor 9. These images will be generally as shown in FIG. 6, image 28 corresponding to the image obtained with the lower energy X-radiation. In this case, the spots corresponding to diamonds, 30 and 30' may be fainter than the spots 29 corresponding to mineral but will still be picked up by processor 9. The images are then processed in a similar way by processor 10 as the second embodiment and as shown in FIG. 7.

In the second and third embodiments, only the area of the shadow produced by the microdiamond is measured and assumptions about the shape of the particle have to be made in order to estimate its weight.

EXAMPLE

An apparatus according to the first embodiment of the invention is set up to observe samples having grain sizes in the range from 50 microns to 300 microns.

A sealed tube X-ray source is used operating at about 9 keV. Beam currents of about 0.1 mA are needed, assuming a source to detector distance of 4 cm. The focal spot may have a size in the range 10 to 600 micrometers, preferably 30 to 300 micrometers depending on the distance from the samples to the camera and the resolution required. A microfocus tube may be needed if a small spot is required.

A silicon CCD camera chip is used to form images of the X-radiation transmitted by the sample, the image being averaged over a number of frames to give adequate image quality. The apparatus is set up to observe one slide every 5 to 10 seconds using a processor provided by a fast personal computer with a frame store card. The computer may be set up to indicate which samples have microdiamonds and to estimate their size and weight, may also indicate where the microdiamonds are on the image using a coordinate system.

The present invention has been described above purely by way of example, and modifications can be made within the invention.

We claim:

1. A method of detecting diamonds in a rock sample, comprising reducing the rock sample to small particles, placing a layer of the particles on a substrate, irradiating the particles with X-radiation, sensing X-radiation transmitted through the layer of particles, and detecting diamonds by their greater transparency to X-radiation than the remainder of the particles.

2. The method of claim 1, wherein an image of the transmitted X-radiation is formed.

3. The method of claim 2, wherein the image of the transmitted X-radiation is formed on an X-ray detector, for giving signals representative of the image.

4. The method of claim 3, wherein the detector is very close to the particles.

5. The method of claim 1, wherein the particles are of a size substantially in the range from 20 to 1000 micrometers.

6. The method of claim 1, further comprising locating the positions of the diamonds.

7. The method of claim 1, wherein the X-radiation comprises soft X-radiation.

8. The method of claim 1, wherein the particles are irradiated with X-radiation from an X-ray point source.

9. The method of claim 1, further comprising irradiating the particles with further radiation different from the first-mentioned radiation and sensing the further radiation transmitted through the layer of particles.

10. The method of claim 9, wherein the further radiation comprises visible radiation.

11. The method of claim 9, wherein a first image is formed comprising an image of the first-mentioned radiation transmitted through the layer of particles, a second image is formed comprising an image of the further radiation transmitted through the layer of particles, and the first and second images are compared.

12. The method of claim 10, wherein the further radiation is such that a lesser proportion of the further radiation is transmitted through a diamond particle than the first-mentioned radiation.

13. The method of claim 10, wherein the further radiation comprises a greater proportion of X-radiation of longer wavelengths than the first-mentioned radiation.

14. The method of claim 11, wherein spots representing particles in the first image and in the second image are identified and compared.

15. The method of claim 1, wherein an image of the transmitted X-radiation is formed, spots representing particles in the image are identified, and the intensity of each spot is sensed.

16. The method of claim 15, wherein the sensing of the intensity of each spot is corrected with reference to the size of the spot.

17. The method of claim 14, wherein spots representing powder particles in the image are identified, and the intensity of each spot is sensed, a spot being identified as produced by a diamond if it is more intense in the second image than in the first image.

18. The method of claim 14, wherein spots representing powder particles in the image are identified, the intensity of each spot is sensed and the intensity of each spot is then corrected with reference to the size of the spot, a spot being identified as produced by a diamond if its corrected intensity in the second image is greater than that in the first image.

19. The method of claim 1, wherein an image of the transmitted X-radiation is formed in such a manner that particles form spots on the image which are darker than the background.

20. Apparatus for detecting diamonds in a rock sample which has been reduced to small particles, comprising means for irradiating a layer of the particles with X-radiation, means for sensing X-radiation transmitted through the layer of particles, and means for detecting diamonds in the layer of particles by the greater transparency of diamonds than the remainder of the particles.

21. The apparatus of claim 20, wherein the sensing means comprises means for forming an image of the transmitted X-radiation.

22. The apparatus of claim 20, further comprising a substrate for mounting the layer of particles.

23. The apparatus of claim 22, further comprising means for storing a plurality of substrates for mounting the layer of particles, and means for feeding the substrates one at a time, from the storing means, to the irradiating means.

24. The apparatus of claim 20, wherein the irradiating means is set up to produce soft X-radiation.

25. The apparatus of claim 20, further comprising automatic means for analyzing the sensing of the X-radiation to detect diamonds in the particles.

26. The apparatus of claim 20, further comprising means for irradiating the layer of particles with further radiation different from the first-mentioned radiation, and means for sensing the further radiation transmitted by the layer of particles.

27. The apparatus of claim 26, and comprising computing means for comparing the sensing of the first-mentioned X-radiation and of the further radiation to detect diamonds in the layer of particles.

28. The apparatus of claim 27, wherein the means for sensing the further radiation comprises means for forming an image of the further radiation.

29. The apparatus of claim 20, wherein the sensing means is arranged to be positioned very close to the layer of particles.

30. The apparatus of claim 20, wherein the irradiating means comprise an X-ray point source.

\* \* \* \* \*